(12) United States Patent
Jovancicevic et al.

(10) Patent No.: US 7,713,405 B2
(45) Date of Patent: *May 11, 2010

(54) QUANTITATIVE TRANSIENT ANALYSIS OF LOCALIZED CORROSION

(75) Inventors: Vladimir Jovancicevic, Richmond, TX (US); Carlos M. Menendez, Houston, TX (US); Paul Hammonds, Katy, TX (US); Wai Yeung Mok, Manchester (GB)

(73) Assignee: Baker Hughes Incorporated, Houston, TX (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/116,003

(22) Filed: May 6, 2008

(65) Prior Publication Data

US 2008/0283418 A1    Nov. 20, 2008

Related U.S. Application Data

(63) Continuation-in-part of application No. 11/086,191, filed on Mar. 21, 2005, now Pat. No. 7,368,050.

(60) Provisional application No. 60/556,644, filed on Mar. 26, 2004.

(51) Int. Cl.
*G01N 17/04* (2006.01)

(52) U.S. Cl. .................. 205/775.5; 204/404

(58) Field of Classification Search ............. 205/775.5, 205/776, 776.5; 204/404
See application file for complete search history.

(56) References Cited

U.S. PATENT DOCUMENTS

| | | | |
|---|---|---|---|
| 3,660,249 A | 5/1972 | Townsend | |
| 3,716,460 A | 2/1973 | Weisstuch et al. | |
| 3,878,064 A | 4/1975 | Weisstuch et al. | |
| 4,238,298 A | 12/1980 | Tsuru et al. | |

(Continued)

FOREIGN PATENT DOCUMENTS

GB    2218521 A    11/1989

(Continued)

OTHER PUBLICATIONS

Searson et al. "Analysis of Electrochemical Noise Generated by Corroding Electrodes under Open-Circuit Conditions," J. Electrochem. Soc. vol. 135, No. 8, pp. 1908-1915, Aug. 1988.*

(Continued)

*Primary Examiner*—Alex Noguerola
(74) *Attorney, Agent, or Firm*—Mossman Kumar & Tyler PC

(57) ABSTRACT

An electrochemical noise method, apparatus and system may be used to estimate and/or calculate parameters of interest related to corrosion rates of an electrically conductive article. The apparatus involves a working electrode (having substantially the same composition of the electrically conductive article), a reference electrode, and a counter electrode in an environment of interest. The working electrode is placed under potentiostatic control. A current transient between the working electrode and the counter electrode is measured. The working electrode is switched to open potential. A potential transient is measured over the duration of a localized corrosion event. The localized corrosion may then be calculated based on the measured potential transient and the current transient.

15 Claims, 14 Drawing Sheets

U.S. PATENT DOCUMENTS

| | | |
|---|---|---|
| 4,395,318 A | 7/1983 | Tait et al. |
| 4,575,678 A | 3/1986 | Hladky |
| 5,139,627 A | 8/1992 | Eden et al. |
| 6,280,603 B1 | 8/2001 | Jovancicevic |
| 6,683,463 B2 | 1/2004 | Yang et al. |
| 6,987,396 B2 | 1/2006 | Yang et al. |
| 7,368,050 B2 * | 5/2008 | Jovancicevic et al. .... 205/775.5 |

FOREIGN PATENT DOCUMENTS

| | | |
|---|---|---|
| WO | 9850786 A1 | 11/1998 |

OTHER PUBLICATIONS

Isaacs et al., "Potential Transients, Transmission and Electrochemical Corrosion Detection," Brokhaven National Labs Conference Proceedings (BNL-48707, Conf-9309150), 1993).*

Legat et al., "Chaotic Analysis of Electrochemical Noise Measured on Stainless Steel," J. Electrochem. Soc., vol. 142, No. 6, Jun. 1995, pp. 1851-1858.

Dorin et al., "Determination of leaching rates of precious metals by electrochemical techniques," J. of Appl. Electrochem. 21, 1991, pp. 419-424.

J.R. Scully, "Polarization Resistance Method for Determination of Instantaneous Corrosion Rates," Corrosion, vol. 56, No. 2, 2000, pp. 199-218.

* cited by examiner

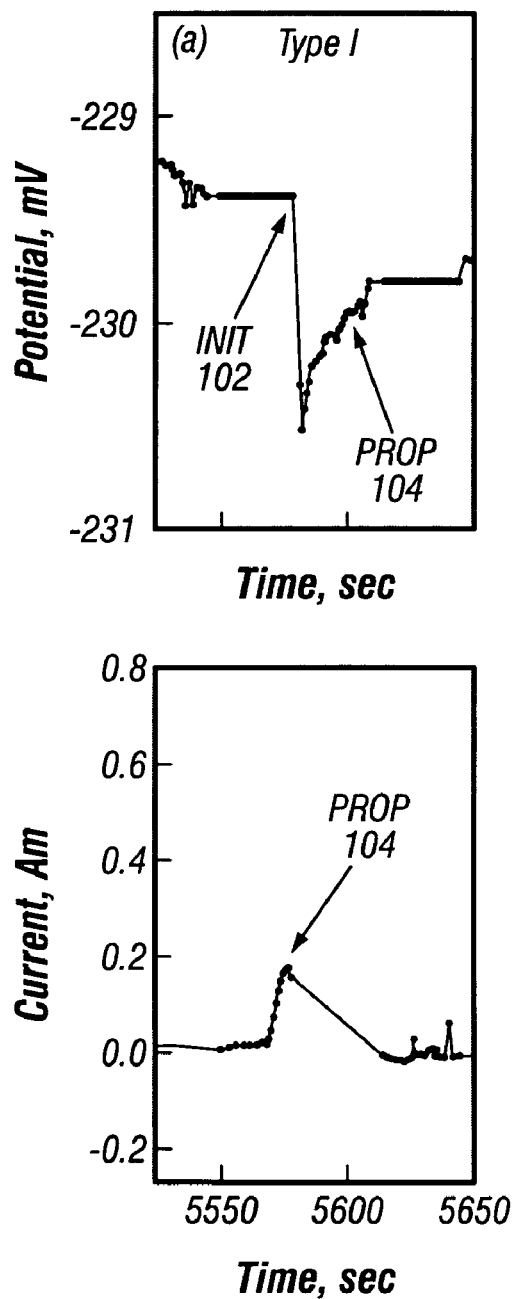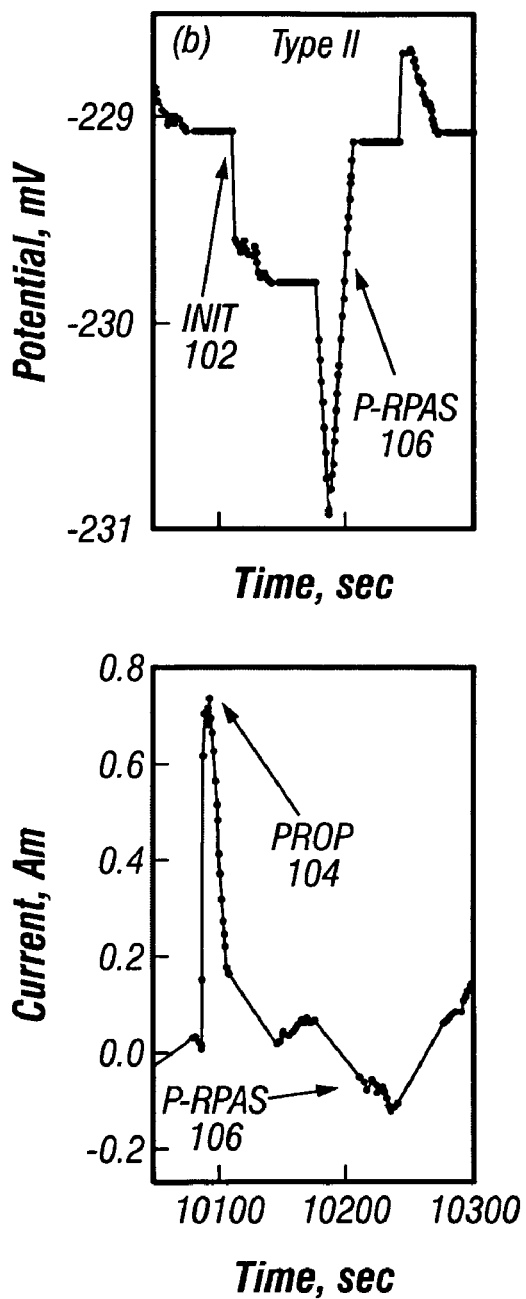
FIG. 1A
FIG. 1B

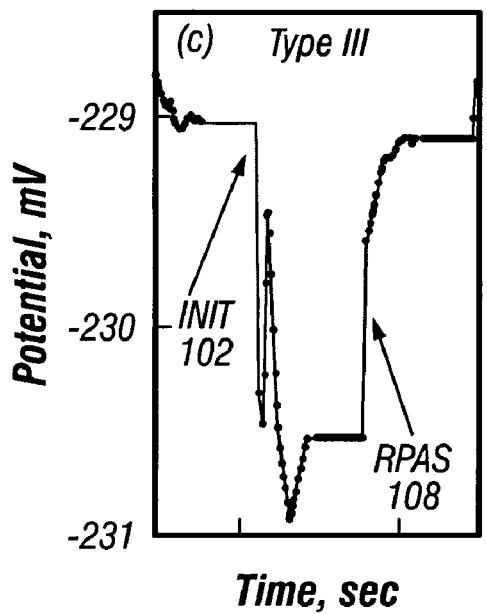
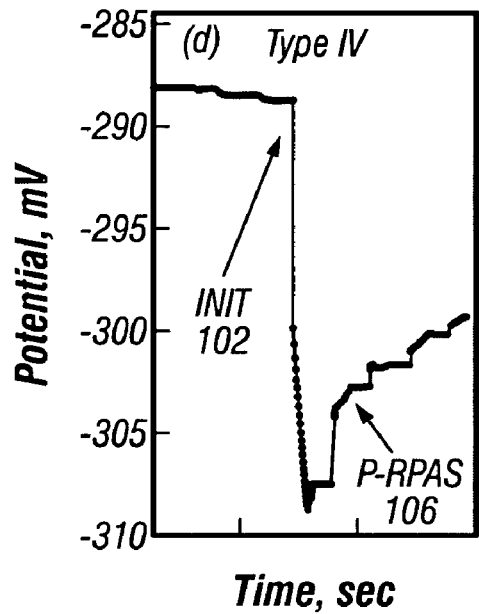
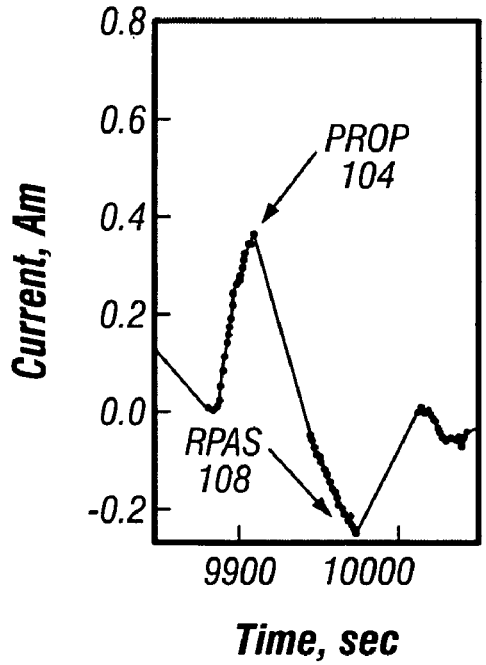
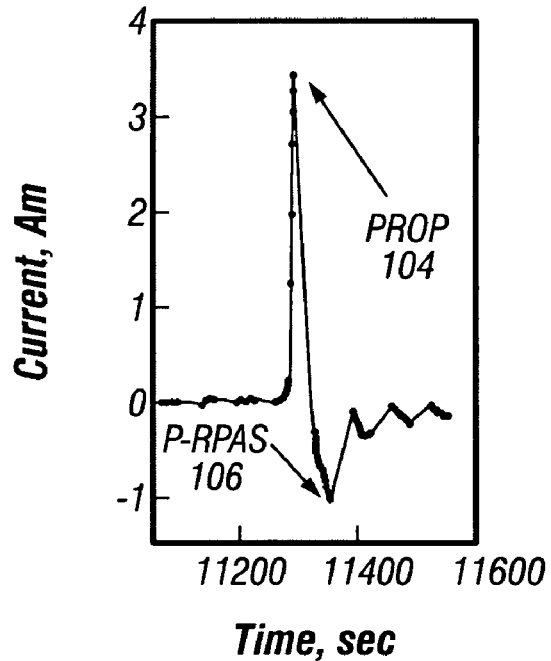
FIG. 1C
FIG. 1D

QUANTITATIVE TRANSIENT ANALYSIS OF LOCALIZED CORROSION

CROSS-REFERENCE TO RELATED APPLICATIONS

This application is a continuation-in-part from U.S. patent application Ser. No. 11/086,191 filed Mar. 21, 2005, which issued May 6, 2008 as U.S. Pat. No. 7,368,050, which in turn claims the benefit of U.S. Provisional Patent Application No. 60/556,644 filed on Mar. 26, 2004.

TECHNICAL FIELD

The present invention relates to an electrochemical noise method and system for estimating and calculating corrosion rate parameters. The invention relates to methods and techniques for evaluating localized corrosion, and most particularly relates in a non-limiting embodiment, to methods and techniques for evaluating localized corrosion in hydrocarbon pipeline, transportation systems, processing vessels and fluid handling equipment.

TECHNICAL BACKGROUND

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants are in the form of localized corrosion. Localized corrosion may result in loss of production, increase in maintenance cost, environmental pollution and potential health and safety hazards, etc. It is important that the occurrence of localized corrosion is identified and the severity determined in advance of structural failure, particularly catastrophic failure. In addition, the ability of chemicals to inhibit localized corrosion needs to be determined.

Localized corrosion is the selective removal of metal by corrosion at small areas or zones on a metal surface in contact with a corrosive environment, usually a liquid. While pitting is a localized corrosion, the locally corrosive pits may eventually cover substantial portions of a corroded electrically conductive article's surface. Localized corrosion may occur when small local sites are attacked at a much higher rate than the rest of the surface. Localized corrosion occurs when corrosion works with other destructive forces such as stress, fatigue, erosion and chemical attacks. Localized corrosion can cause more damage than any of these destructive forces individually.

The problems resulting from localized corrosion have been dealt with for many years with variable success. Localized corrosion is highly stochastic in nature and its occurrence is fairly unpredictable. Thus, it is critical that statistical analysis is carried out when studying or monitoring localized corrosion. Currently, localized corrosion is studied or monitored by measuring directly large features (e.g. pits) on the surface by using standard optical microscopy with limited spatial resolution. Indirect methods are also used, such as electrochemical noise, to provide indication of the probability of localized (e.g. localization index) corrosion.

Electrochemical noise (ECN) may be defined as the spontaneous fluctuations of current and potential generated by corrosion reactions. Various methods have been used to determine corrosion rates, including a linear polarization resistance (LPR) method. In LPR a direct current (DC) signal is applied to a corroding cell consisting of two or three electrodes and the resulting DC polarization is monitored. Provided that the applied current is small that the potential shift is less than 20 millivolts (mV), the response is linear in most cases and the measured resistance, commonly known as the polarization resistance, may be related inversely to the rate of the uniform corrosion attack. Other techniques include the application of electrochemical impedance spectroscopy (EIS) in which a sine wave current or potential is applied. In a similar manner to the linear polarization technique, and the sine wave potential or current resulting from the applied current or potential is monitored. Alternatively, a pseudo random noise signal can be applied to a corroding cell, with the electrochemical impedance obtained by time or frequency domain transformations.

Although the above techniques are widely employed, they: (1) possess limitations in that they only provide information on uniform (general) corrosion conditions because they provide an average signal for the surface of the electrode being monitored; and (2) depending upon the environment, metallic material, and corrosion type, the assumption that the corrosion rate is inversely proportional to the measured charge transfer or polarization resistance is invalid because the corrosion is of a localized nature. These problems have been addressed by monitoring localized corrosion via the utilization of electrochemical potential noise analysis. Alternatively, by coupling current analysis with electrochemical potential noise analysis further information can be obtained. For example, two similar electrodes can be coupled together via a zero resistance ammeter with the output of the zero resistance ammeter passed to the input of the electrochemical noise analysis system. In this way, the fluctuation of the coupling current may be analyzed in essentially a similar manner as for the electrochemical potential noise analysis described previously.

U.S. Pat. No. 5,139,627 to Eden et al. discloses a system which employs two working electrodes fabricated with the same material and exposed to the same corrosion conditions as the metallic surface to be tested. This system further employs a device for measuring the coupling current between the working electrodes, a device for measuring electrochemical potential noise originating from the electrodes, and a device for comparing the coupling current with the electrochemical current noise to provide an output indicative of the degree to which corrosion is localized. Eden et al. utilize open circuit potential conditions, employing two working electrodes in an electrolyte environment wherein both electrodes are short circuited with a low resistance amp meter. The current between these two working electrodes is the result of corrosion occurring on them, with the measurement of the net current relating to the corrosion on both of them. Disadvantages of this system, however, range from the fact that the working electrodes need to be identical to obtain accurate readings and obtaining such identical electrodes is difficult, if not impossible, another problem is that it is unknown which electrode is responding to reveal the corrosion, due to the fact that this system requires the use of two working electrodes which limits where this system can be employed. Furthermore, distinguishing between various types of localized corrosion is, at minimal, difficult due to the fact that both electrodes contribute to the system response.

What is needed in the art is a simplified corrosion rate detection system and method. The methods of the present invention overcome some disadvantages of the prior art by providing corrosion detection estimation capability for metal corrosion.

SUMMARY

There is provided a method, apparatus and system for calculating a non-exhaustive list of localized corrosion parameters for an electrically conductive article including: number of corrosion events, event duration, frequency, rate of penetration, area, volume of metal displaced, mass, type of transient, and whether passivation occurs or not. The method involves: placing a working electrode, a reference electrode, and a counter electrode in an environment of interest, wherein the working electrode has substantially the same composition as the electrically conductive article; placing the working electrode under a potentiostatic control; and measuring a current transient between the working electrode and the counter electrode. Switching the working electrode to an open circuit potential mode. A potential transient is measured substantially over a duration of a localized corrosion event. The localized corrosion parameters may be calculated directly from analysis of current and potential transients and the current transient. The parameters may include i) the rate of penetration of a pit, based on a time rate of change of the monitored transient; and ii) a rate of penetration for multiple pits, based on a sum of ratios:

$$\frac{1}{R} = \sum_{n=1}^{n} \left(\frac{1}{R_n}\right)$$

where each $R_n$ is given substantially as $$R_n(t + \Delta t) = R(t + \Delta t) \cdot \frac{\sum_{n=1}^{n} PD_n^2(t)}{PD_n^2(t)}.$$

There is also provided in one non-limiting embodiment, an apparatus for determining the localized corrosion of an electrically conductive article which includes a working electrode having substantially the same composition of the electrically conductive article, a reference electrode, a counter electrode, and at least two sensors. One sensor is for measuring the current transient between the working electrode and the counter electrode until initiation of a current transient due to a localized corrosion event, where the current transient is measured substantially over the duration of the localized corrosion event. Another sensor is for measuring potential transient data between the working electrode and the reference electrode until initiation of a potential transient due to a localized corrosion event, where the potential transient is measured substantially over the duration of the localized corrosion event. The apparatus also includes a processor for calculating the localized corrosion from the measured current transient and potential transient data, including one or both of parameters i) and/or ii) noted above.

In another non-restrictive version, there is provided a localized corrosion measuring system for an electrically conductive article in an environment of interest, which system includes an electrically conductive fluid-conduit composed of a material of interest, a working electrode which is substantially composed of the material of interest, a counter electrode, a reference electrode and a measurement system connected to the working electrode, the counter electrode, and the reference electrode for monitoring transient events indicative of localized corrosion. The transient events are monitored between the working electrode, the counter electrode and the reference electrode substantially over the duration of the transient events. A corrosion parameter such as i) and/or ii) described above may be calculated from these data.

The localized corrosion rate may be a function of the frequency of potential and current transients measured over time; the amplitude of potential and current transients measured over time; the duration of potential and current transients over time; or the distribution of potential and current transients over time. The corrosion rate may also be determined directly from the current transient measurements. For potential transients, the corrosion rate may also be estimated by converting the potential into equivalent current data or via the application of double layer capacitance and potential relationship. The method and apparatus herein may also involve estimating the localized corrosion rate of an electrically conductive article by a ratio of a standard deviation of potential and a standard deviation of current.

The method and apparatus described herein may be implemented as a set of computer executable of instructions on a computer readable medium, comprising ROM, RAM, CD-ROM, Flash RAM or any other computer readable medium, now known or unknown that when executed cause a computer to implement the functions described.

Examples of the more important features thus have been summarized rather broadly in order that the detailed description thereof that follows may be better understood, and in order that the contributions to the art may be appreciated. There are, of course, additional features that will be described hereinafter and which will form the subject of the claims appended hereto.

BRIEF DESCRIPTION OF THE DRAWINGS

For detailed understanding of the present invention, references should be made to the detailed description of various disclosed embodiments, taken in conjunction with the accompanying drawings, in which like elements have been given like numerals, wherein:

FIG. 1A-1D illustrate types of transients representing localized corrosion events;

DETAILED DESCRIPTION

Figure 2A:
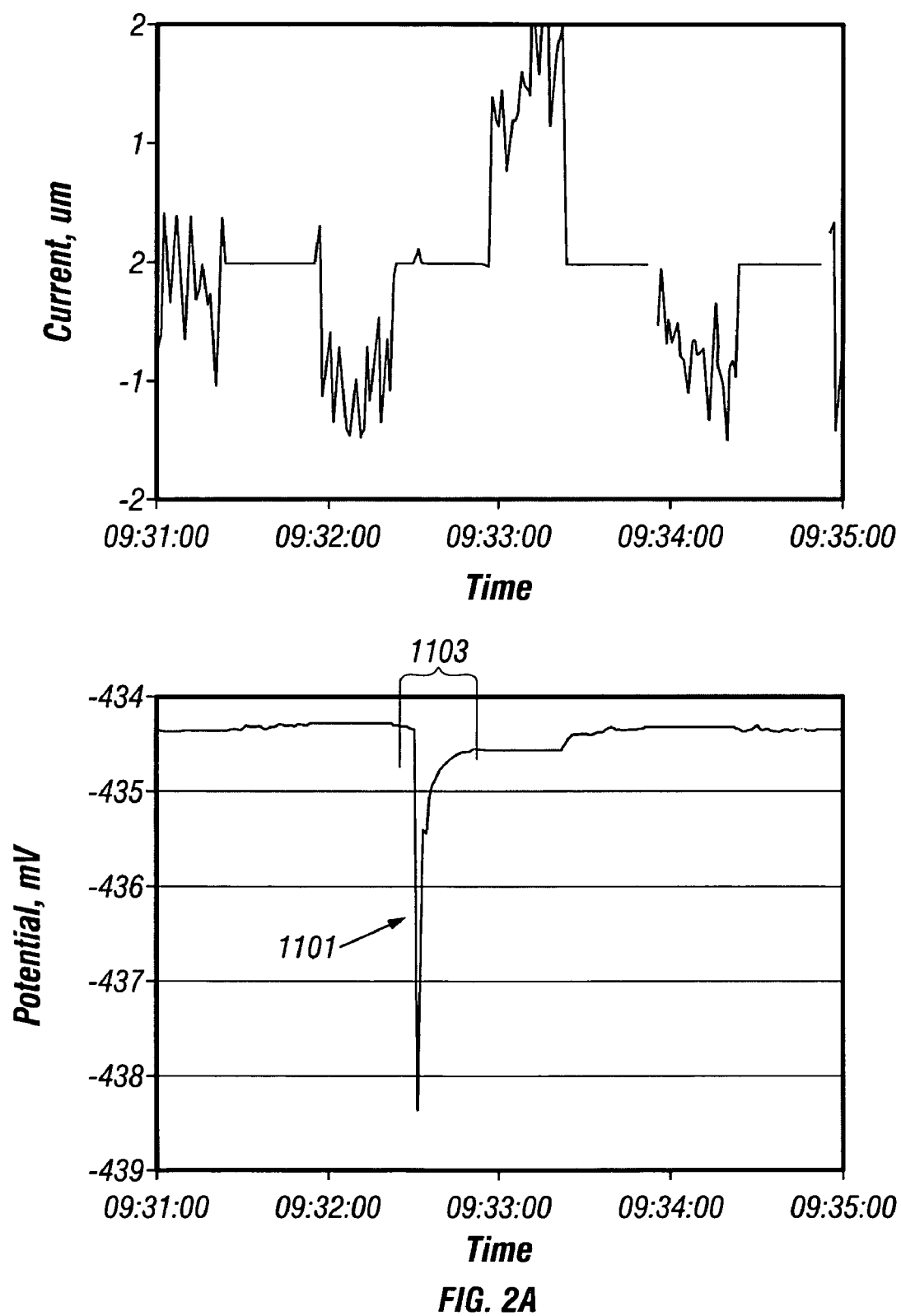
FIG. 2A illustrates transients of potential and current measurement cycles for a 30 second half-period data acquisition system.

A method and apparatus have been discovered for the detection and characterization of the corrosion behavior in systems where localized corrosion predominates (in the form of pitting) and is quantitatively evaluated. The severity, frequency and time/space distribution of the localized events are determined from potential and current measurements recorded from the corroding systems. Localized Corrosion Monitoring (LCM) using the current and potential transient analysis methods provided in the present example are performed by the disclosed control and analysis methodology. The present example provides for continuous corrosion monitoring and real time analysis of the monitored data. Real-time system monitoring of the corrosion status of operating equipment is enabled. In laboratory investigations, the method and apparatus provide information on localized corrosion behavior that may be directly correlated with corrosion attacks.

The method and apparatus herein provide continuous monitoring of the sudden changes in both the corrosion potential and current with time and can provide information about localized corrosion rate and processes. These changes develop dynamically in the form of transient responses in potential or current measurements. While numerous methods have been used to measure general corrosion (e.g. linear polarization resistance, electrical resistance, EIS), there have been few analysis methods for characterizing localized corrosion.

The current analysis of localized corrosion based on electrochemical noise provides indications of the likelihood of localized corrosion (Localization Index, $LI=\sigma_i/rms_i$) without specific reference to the surface affected, or the number and distribution of those localized events. LI relates to the degree of localized corrosion compared to general corrosion, i.e., the greater the LI the higher the probability of localized corrosion.

U.S. Pat. No. 6,280,603 to Jovancicevic discloses a potentiostatic electrochemical noise (P-ECN) invention (which patent is hereby fully incorporated herein by reference) and provides quantitative measure of localized corrosion in terms of type, frequency, distribution and penetration rate. Three different types of single current/potential transients: (i) initiation/propagation (Type I), (ii) initiation/partial repassivation (Type II), (iii) and initiation/repassivation (Type III), and one multiple initiation/propagation (Type IV) transients are recorded over time (FIG. 1 in Jovancicevic). The transients may be defined as a sudden cathodic shift in potential or anodic shift in current at open-circuit or constant potential, respectively. For an example system of objects to be monitored, depending on the metal or material examined, a transient may be a potential shift of $\geq 0.5$ mV/sec or an anodic shift of $>0.1$ $\mu A/cm^2$/sec. For some typical systems, the Type I and II transients may be chosen as transients that last, for example, $\leq 5$ seconds, while Type III transients may be chosen as those that last between 200 seconds and $\geq 30$ seconds and Type IV as those that last $\geq 200$ seconds. The relative differences of the amplitudes and frequencies of various transients may be indicative of the types of corrosive attacks present in any active system. These electrochemical noise data can provide an indication of the type of corrosion damage occurring; and may be used to indicate the nature of localized attack. The severity of localized corrosion may be measured by the penetration rate of individual pits.

Based on the magnitude, duration and relative rate of decrease and/or increase of potential and current signals, four different types of transients can be observed in the LCM time records and classified as: Type I initiation/propagation (IP), Type II initiation/partial repassivation (IPR), Type III initiation/repassivation (IR) and Type IV initiation/repassivation/propagation (IRP) transients. Types I and II are termed 'active' because pitting is occurring during the corrosion events. Type III is of less concern because the site of the corrosion undergoes repassivation. Type IV transients are indicative of multiple pits occurring that are generally very large in number, more or less active, uniformly distributed, smaller and shallower than the IP (Type I) and IPR (Type II). This transient analysis of the potential/current time dependence will be used in quantifying localized corrosion activity on the carbon steel and stainless steel tests.

TYPE I: Potential IP transients are characterized by a sudden decrease in open-circuit potential, i.e. pit initiation (1-3 sec), followed by a slow increase in potential (>30 sec), i.e. pit propagation, close to or lower than its original value. An example of Type I is illustrated in FIG. 1A. The typical decrease in potential is <3 mV. The corresponding current transients, whether preceding or following the potential transients can vary significantly depending on the localized corrosion activity (0.1-100 $\mu A$). The lower the ratio of the magnitudes of potential and current transients (Rt), the more active the pit and greater the area affected. A typical potential/current IP transient is presented in FIG. 1A showing sharp decrease (pit initiation: INIT 102) and subsequent slow increase (pit propagation: PROP 104) in potential accompanied with the current peak. Pits that grow by this mechanism are generally very active, non-uniformly distributed, large and deep.

TYPE II: Potential IPR transients can be described in terms of sudden decrease in open-circuit potential (<3 mV) followed by a slow increase in potential to, higher or lower than the initial open-circuit potential. These transients can extend over much larger time periods (>1000 sec) compared to the potential IP transients. The corresponding current transients show both larger current initiation (increase) and lower current partial repassivation (decrease), signals. The typical current increases during these transients are <10 $\mu A$. FIG. 1B depicts one of the IPR potential/current transients showing pit initiation (INIT 102) and partial repassivation (P-RPAS 106). Pits formed by the IPR mechanism are generally active, more uniformly distributed, smaller and shallower.

TYPE III: Potential IR transients can be characterized by a rapid and generally larger decrease in potential (2-100 mV) associated with an equally fast increase in potential to its original value within few free potential/potential hold cycles. The corresponding current transients (<1-2 $\mu A$) show equally strong positive (initiation INIT 102) and repassivation, RPAS 108, signals as illustrated in FIG. 1C. Typical IR transients are associated with passive, numerous, and uniformly distributed extremely small pits.

TYPE IV: Potential IRP transients can be described in terms of a steady and large decrease in potential (10-50 mV) followed by a slow increase in potential to a level that is significantly lower than the initial open-circuit potential. These potential transients extend over much larger time periods (1-10 cycles) compared to the potential IP, IPR and IR transients. The IRP current transients show generally successive repassivation and propagation associated with multiple localized corrosion events. FIG. 1D illustrates one of the IRP transients showing pit initiation INIT, and repassivation P-RPAS 106, and continuous propagation of a number of transients. Pits formed by the IRP mechanism are generally very large in number, more or less active, uniformly distributed, smaller and shallower than the IP and IPR.

The occurrence and amplitude of current/potential transients with time are directly related to the number, magnitude (depth) and distribution of localized corrosion events (e.g., pits). Thus, as the transients are longer, and as the amplitudes of the transients are larger, the larger the area effected by corrosion. Also when an area affected by corrosion is larger, the depth of the corrosion is less.

In practice, both the raw current and potential values are checked against a threshold level in order to detect pitting "events". Threshold values (for current and potential) may be specified in terms of offsets from the calculated or determined means. A mean value may be calculated for a half cycle (ignoring any points that are inside a "settling period" as a transient recovers). Each sample is compared against a limit, which is calculated from: mean−threshold (for potential) or mean+threshold (for current). If a value exceeds this limit for both current and potential half-cycles, a detection routine may, as an example, log the following: a) a value of 1 for the count of events in the half cycle; b) the value of the threshold property (e.g., −2.0 mV); and c) the difference of the threshold above (or below for potential) the mean value in the half cycle.

By correlating data acquired from monitored systems with the above parameters, information on the severity and the feature of corrosion damage on the monitored objects may be obtained. Similarly, the effectiveness of corrosion control measures, such as chemical inhibition, may be determined.

Both potential and current LCM data may be acquired by alternatively recording with time using, for example, 30 seconds on (current) and 30 seconds off (potential) potentiostatic control/open circuit potential sequence. However, the entire transient on the current and potential sides may be measured to determine pitting parameters so that charge, mass and volume displaced from localized corrosion pits may be estimated or calculated. (Potential transients may be converted into equivalent current transients by using Ohm's Law, via which the charge can be estimated. An alternative approach to estimate the approximate charge of a potential transient is via the double layer capacitance and potential relationship.) Therefore, operator intervention and/or software may be used to both recognize the onset of current transients (or potential transients), and to begin or resume the alternate cycling after transients have substantially terminated. LCM relies on the measurements of time of occurrence, magnitude, duration, frequency and distribution of distinct potential (negative) and current (positive) transients as a result of initiation and/or propagation/repassivation of localized corrosion events (e.g. pitting, crevice).

Figure 2B:
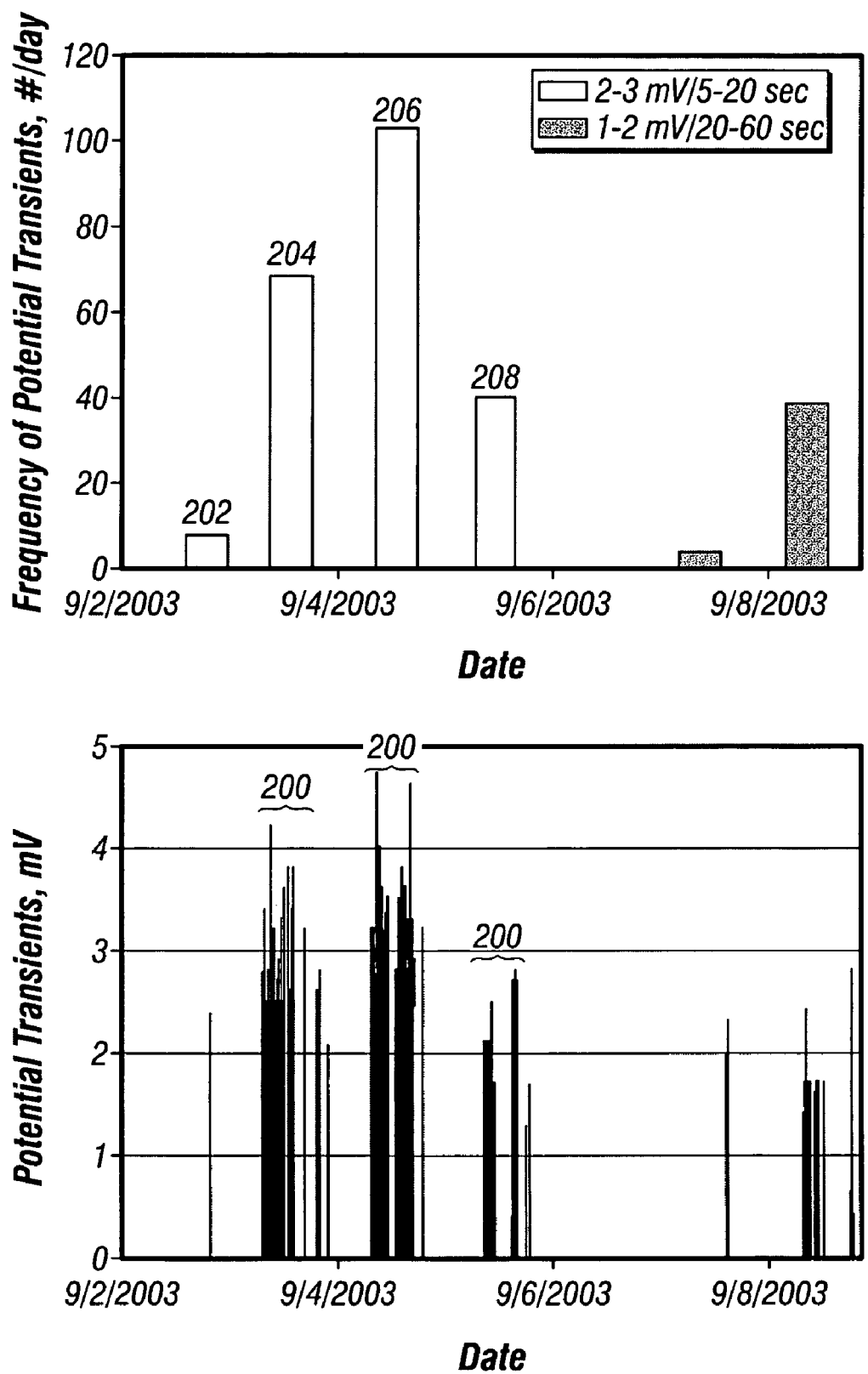
FIG. 2B illustrates normalized frequency data over an experimental period.

FIG. 2A illustrates a typical potential transient 1101 over a time period of approximately 20 seconds 1103 and illustrates the relationship of potential and current measurement cycles for a 30 second half-period data acquisition system. FIG. 2B is a frequency plot of normalized frequency over an experimental period of several days. Overall, the amplitude of the potential transients is typically between 1 to 4 mV, and the majority was >2 mV, as illustrated in FIG. 2B. (It should be noted that frequency illustrated in FIG. 2B was normalized to reflect that half of the LCM measurement cycle was under potentiostatic control operation.) The occurrence or the frequency of these characteristic transients initially increased with time and peaked on day 3 of the test. The frequency then showed a decreasing trend and was at the minimum on day 5. A reverse back to an upward trend was then observed at the end of the test. The frequency of the transients showed tendency of clustering in time and space, indicating the localized nature of these events (grooves, pits). Clusters of transients 200 separated in time indicate separate areas of corrosion. This is illustrated in FIG. 2B, after Day 1 (202) with a cluster of transients in the vicinity of Day 2 (204) representing one area of corrosion, another cluster of transients in the vicinity of Day 3 (206) representing another area of corrosion and still a third area in Day 4 (208) representing a third area of corrosion. The number of clusters of transients utilizing this method is equal to the number of areas of localized corrosion.

Figure 3:
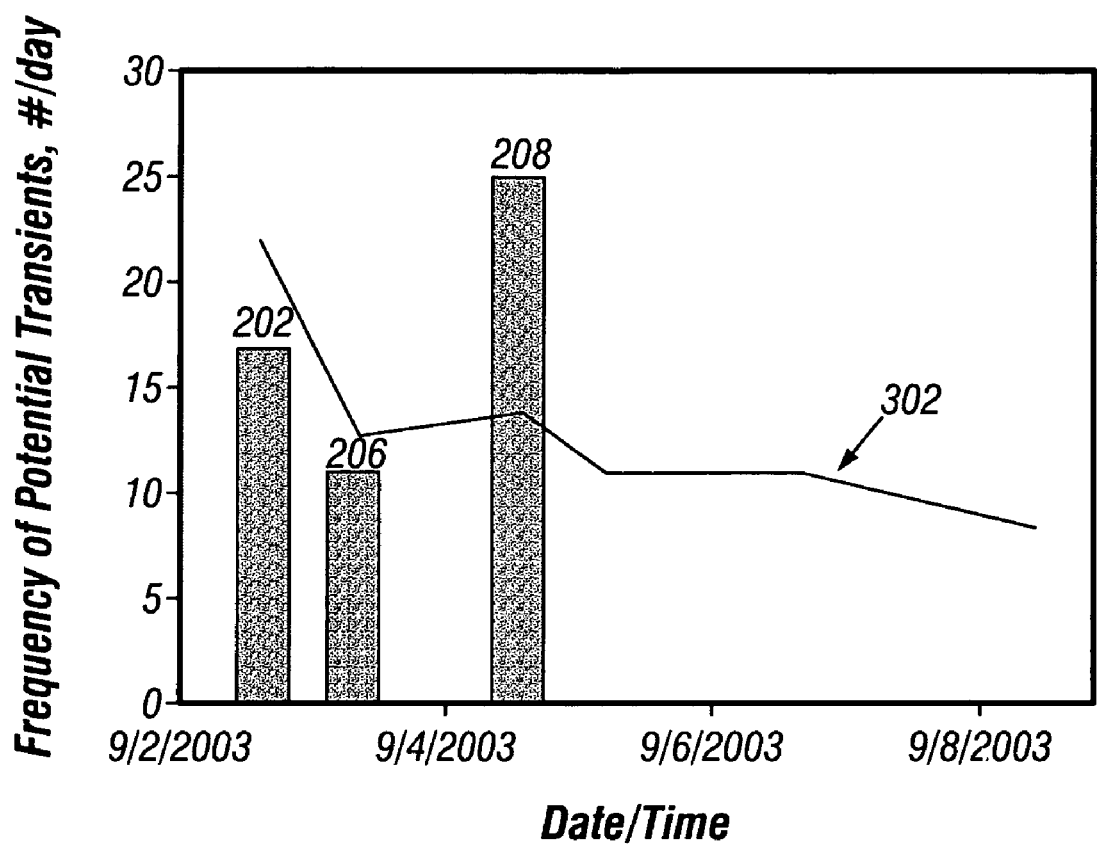
FIG. 3 illustrates the results of calculations of the corrosion rate.

Calculations of the corrosion rate 302 on the first 3 days of the test suggested a rate between 11 to 25 mpy (0.27-0.64 mm/yr), as illustrated in FIG. 3. (The calculations were based on the full surface area of the test electrode, 7.85 cm$^2$.)

Figure 4:
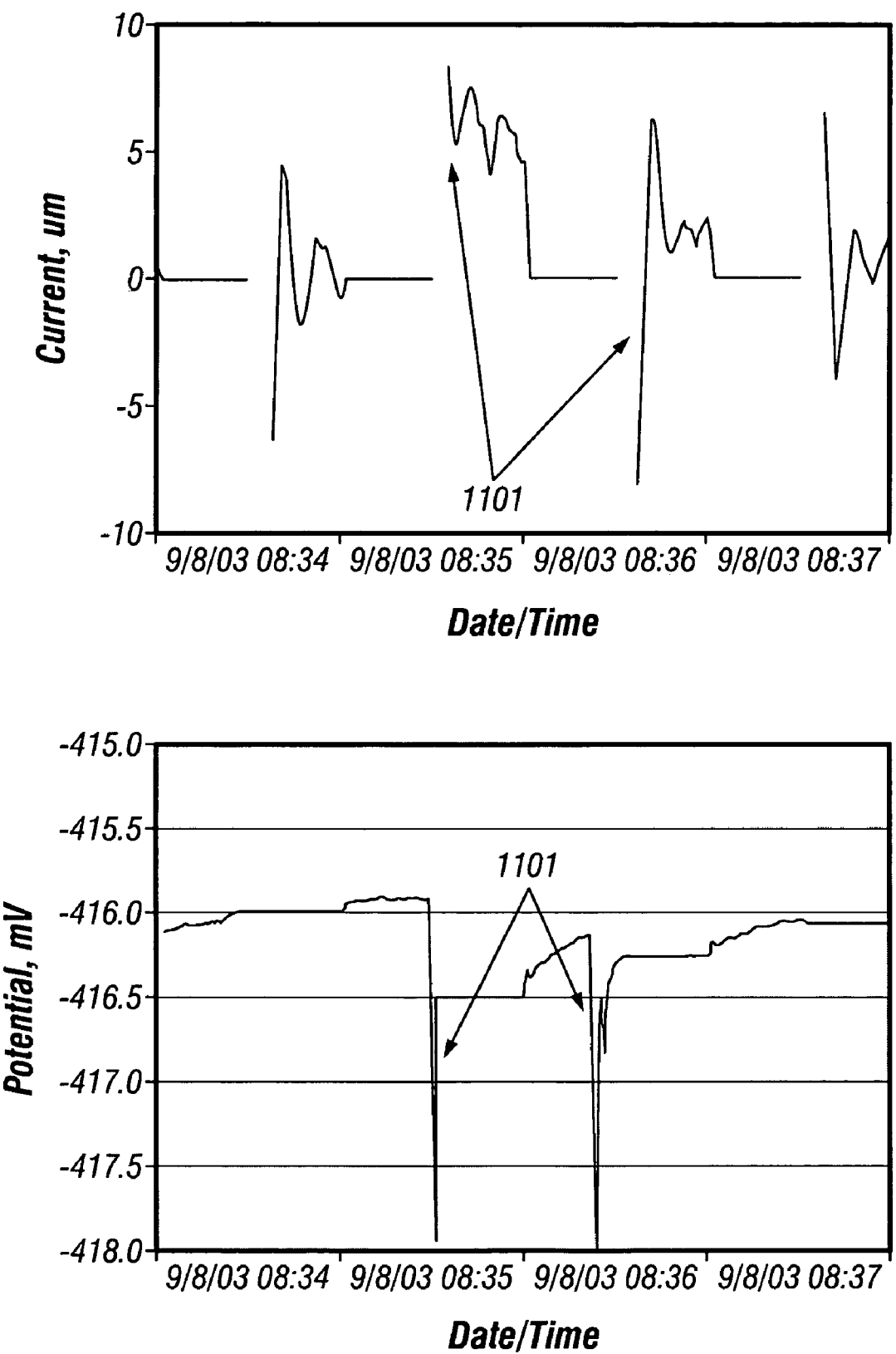
FIG. 4 illustrates episodes of localized activities with the data recorded.

Episodes of localized corrosion activities are clearly evident with the data recorded, as illustrated with transients 1101 in FIG. 4. Examination of the test electrode in this case suggested that corrosion damage was mainly in the form of deep cut groove-like pits (e.g., length 5-37 mm, width 190-380 μm and depth 60-80 μm). There were also a number of isolated pits with similar extent of penetration. The observation suggested that although the corrosion was in the form of localized corrosion, it was not the classical form of localized attack as in the case of pitting. As the LCM data confirmed, the occurrence of two types of localized events (larger but shorter initial transients and smaller but longer transients toward the end), and this correlated with the observation of the groove damage followed with isolated pits formation on the surface of the test electrode.

An example of the LCM technique is illustrated by measurements of the exposure of carbon steel grade C1018 (UNS G10180) in 0.1% sodium chloride (NaCl) solution containing 100 ppm nitrite (in the form of sodium nitrite), at a constant temperature of 50° C. Alloy 276 (UNS N10276) material was used as reference and counter electrodes. Prior to immersion into the test solution, the carbon steel electrode was polished to 1200 grit surface finish, degreased, rinsed with water followed by acetone and dried with air. The carbon steel test electrode was then immersed into the test solution and the corrosion behavior was monitored throughout the duration of the exposure test. The surface morphology of the carbon steel test electrode after the test was then examined using an optical microscope to determine the extent and type of corrosion damage.

Figure 5:
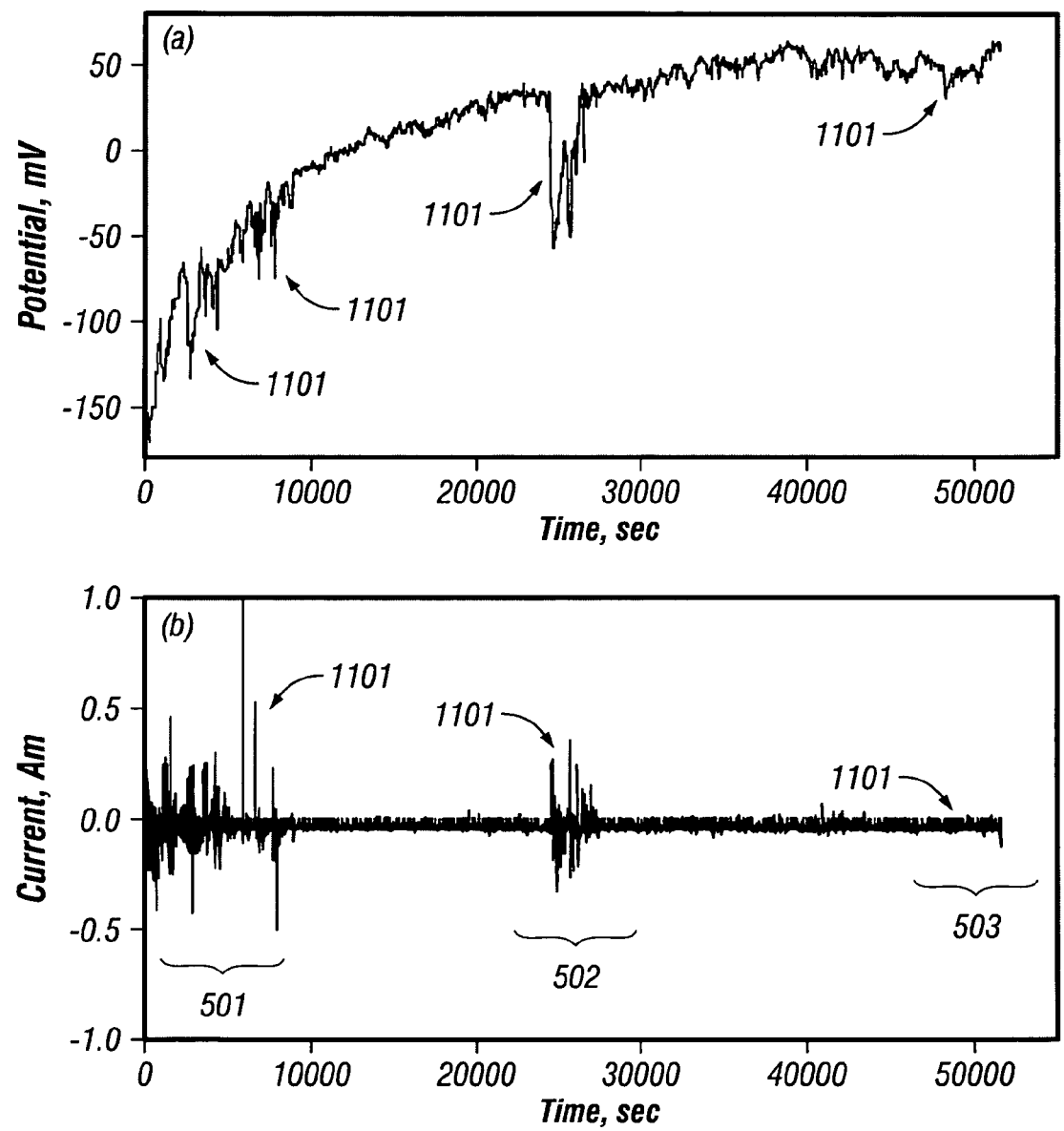
FIG. 5 illustrates episodes of localized activities with the data recorded.
Figure 6:
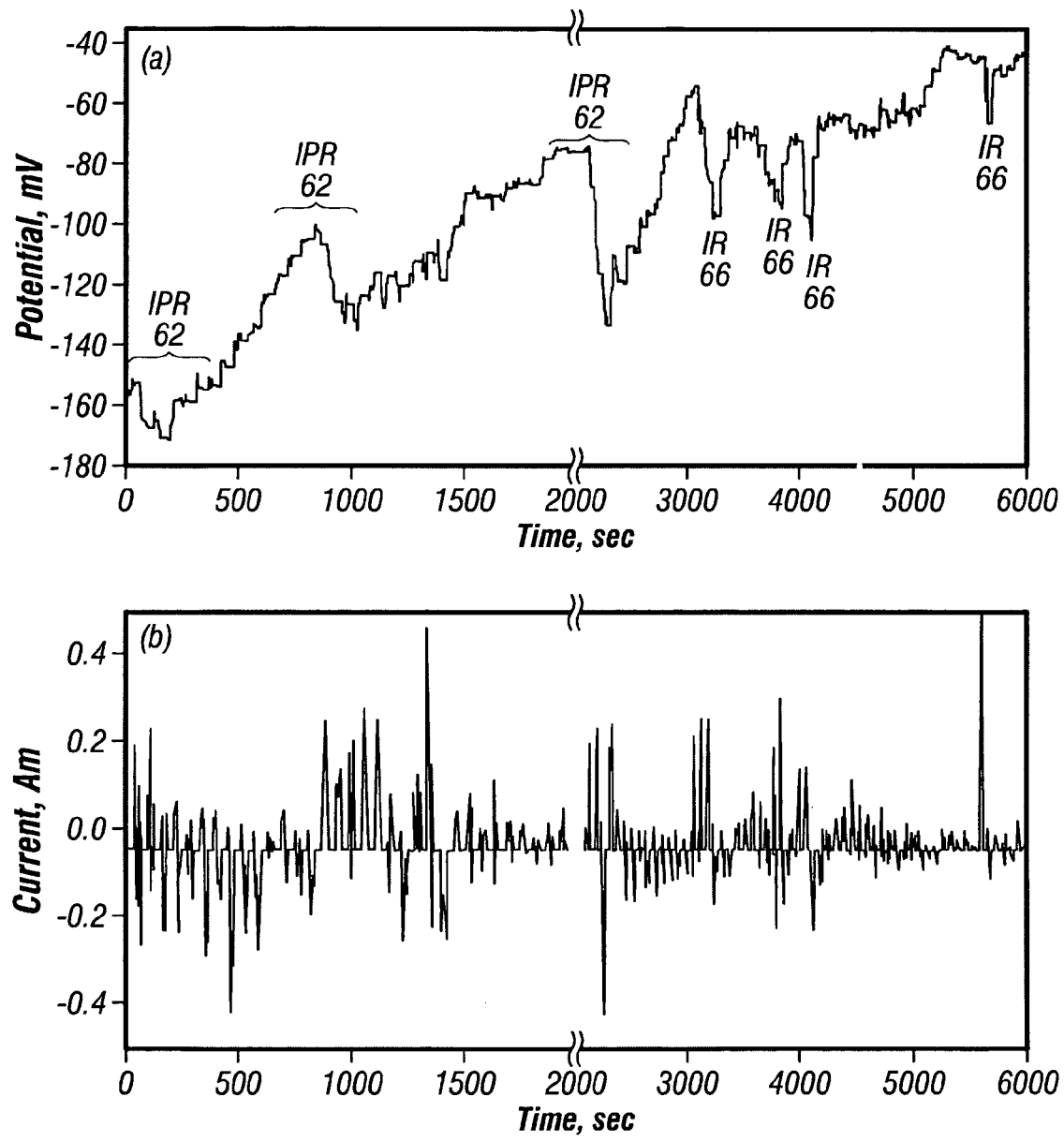
FIG. 6 illustrates data with periods of numerous distinct potential IPR (active) and IR (passive) transients.
Figure 7:
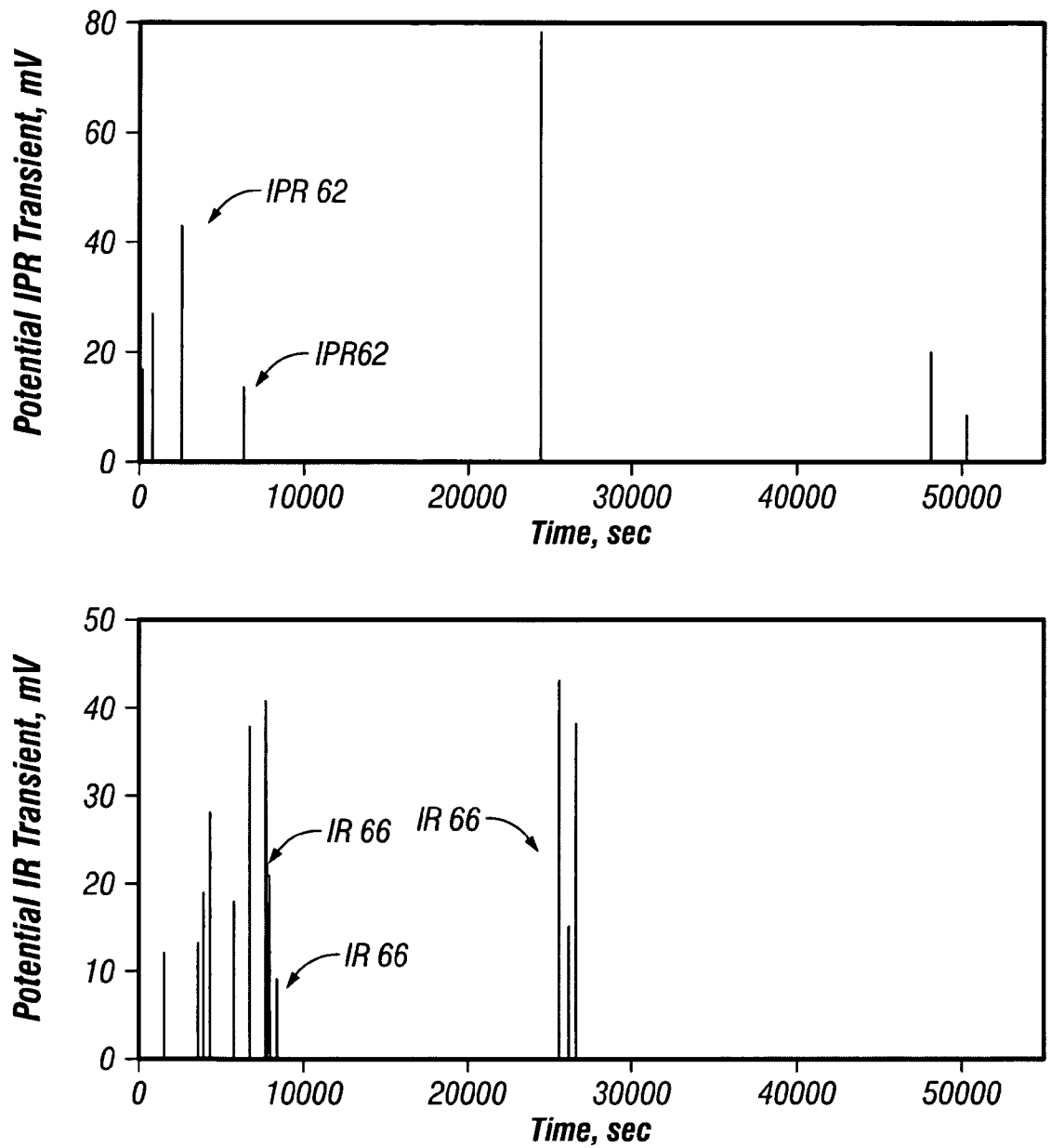
FIG. 7 illustrates data from potential IPR and IR transients.

In this system, partial passivation of the carbon steel electrode was expected because of insufficient amount of nitrite used (100 ppm) in the test solution. Detailed examination of the time records of both potential and current data measurements illustrate periods of localized corrosion activities. Localized corrosion is indicated by the presence of transients 1101 in FIG. 5. These data reveal three periods of significant pitting activities (<8000 sec 501, 23000-27000 sec 502, 47000-51000 sec 503). During these first two time periods numerous distinct potential IPR 62 (active) and IR 66 (passive) transients were observed (FIG. 6), while only two IPR transients were recorded in the latter part of the test. FIG. 7 shows 7 potential IPR 62 and 13 IR transients with 3 IPR 62 transients preceding 7 IR 66 transients and 2 other IPR transients preceding 6 remaining IR transients.

Figure 8:
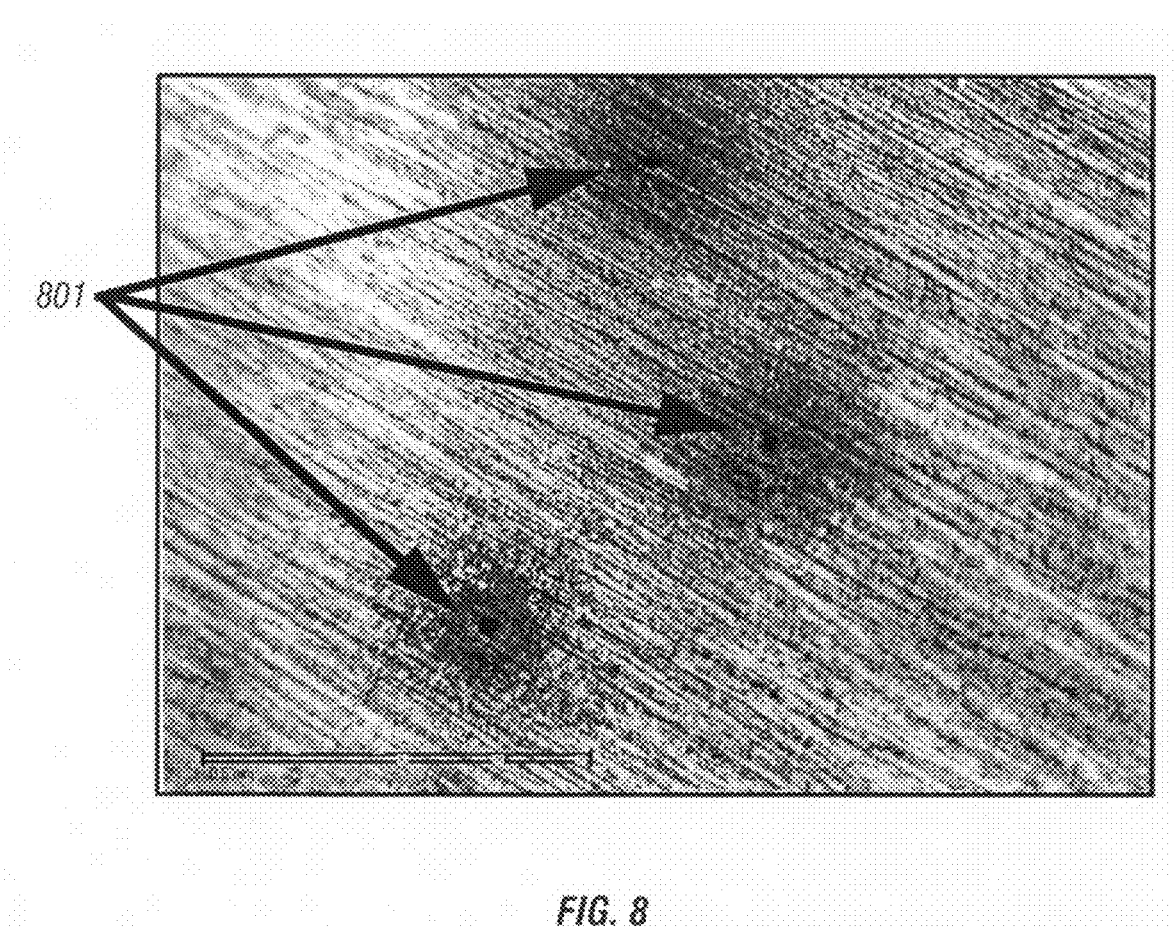
FIG. 8 illustrates pitting as seen on the surface resulting from the events recorded for FIG. 6 and FIG. 7.

These data may be compared with the detailed microscopic examination of the surface of the test specimen with regard to localized corrosion, i.e. presence and nature of pits 801 as shown in FIG. 8. There were altogether 5 larger pits surrounded by greater number of smaller secondary pits and possibly 5 smaller incipient pits. Three of the large pits were in close proximity of each other. The pit depths were within 4-6 μm. The surface morphology showing 5 distinct pits with unspecified number of small pits are in good agreement with the number of potential IPR transients (5) and IR transients (10) recorded. The additional IPR (3) and IR (2) transients that occurred much later in the test are probably 5 small pits observed under the microscope.

Figure 9:
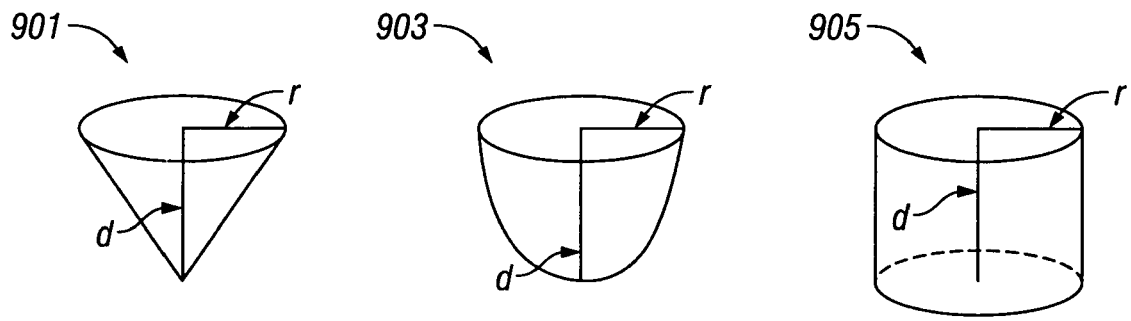
FIG. 9 illustrates schematic views of possible pit geometries.

Using the measurements of the current transients, the volume and or mass of the pit may be determined by integrating Q, where Q=I*t, and Q is charge, I is current and t is time. (The equivalent charge of a potential transient may also be estimated by either converting the potential data into current data via Ohm's Law and followed by integrating the current over time as suggested above, or it can be determined by $Q=C_{dl}*\Delta E$, where $C_{dl}$ is the double layer capacitance and $\Delta E$ is the maximum potential change of the transient.) FIG. 9 illustrates schematically a few of the various types of pit geometries (cone 901, hemisphere 903 and cylinder 905) that may be determined based on Q from the transient current responses. The volume of the material removed due to the pit may be determined using the radius, r, and the depth, d, of the pit and making straightforward assumptions of the geometry of the pit as indicated from the transient responses. The present method provides for estimating the depth of the pit based on the transient data and in combination with potential noise and current noise data to estimate the pit growth. This analysis presumes localized corrosion being the predominant type of corrosion (e.g., oil and gas production, handling and transportation environments).

Q is the electric charge passed by current I over time period t. Current is the rate at which charge passes; therefore $I=\Delta Q/\Delta t$. The charge Q is also related to the quantity of metal lost from the electrode during corrosion (by Faraday's Laws). Hence a knowledge of I and t lead to charge Q and hence metal loss rate. As current I is continually varying then the current is integrated over the time interval t in order to gain information on the charge passed and hence the quantity of metal being lost (corroded).

Various types of transients may be differentiated by type as described above. The current response allows the determination of an initiation of a transient, the type of transients (and type of pitting). For localized corrosion events, cathodic current response is related to an individual pit event or occurrence and the type of transient (Types I-IV) allow for determination of whether repassivation has or will occur, or whether corrosion is halted or continuing.

The method and apparatus herein allow for determination of the volume or mass of metal lost during localized corrosion pitting events. The mass loss during the first pit formation may be determined as $$m_1(g) = \frac{Q \cdot A_{Me}}{z \cdot F} \quad (1)$$

where:
 Q—charge (coulombs)
 m—mass loss (g)
 $A_{Me}$—atomic weight of metal (g/mol)
 z—valency change for metal
 F—Faraday constant=96500 Coulombs/mol The charge, Q, for each pit is calculated as an integral of the area under the current/time curve (transient) as $$Q = \Sigma i \cdot \Delta t \quad (2)$$

Assuming the pit is in the form of hemisphere, the initial pit depth (t=0) of the pit #1 is $$PD_1 = \sqrt[3]{\frac{3 \cdot Q \cdot A_{Me}}{2 \cdot z \cdot \pi \cdot F \cdot \rho_{Me}}} \quad (3)$$

where:
 PD—pit depth
 $\rho_{Me}$—density of metal

Pit #1 growth rate at time t+Δt is calculated by using the noise resistance at time t+Δt($R_{t+\Delta t}=\sigma_v/\sigma_i$) as $$PD_1(t+\Delta t) = PD_1(t) + \frac{A_{Me} \cdot B \cdot \Delta t}{2 \cdot z \cdot F \cdot \pi \cdot \rho_{Me} \cdot R(t+\Delta t) \cdot PD_1^2(t)} \quad (4)$$

Pit #1 growth rate after pit #n formed at time (t+Δt) is calculated by assuming that $$R_1(t+\Delta t) = R(t+\Delta t) \cdot \frac{\sum_{n=1}^{n} PD_n^2(t)}{PD_1^2(t)} \quad (5)$$

and is given by $$PD_1(t+\Delta t) = PD_1(t) + \frac{A_{Me} \cdot B \cdot \Delta t}{2 \cdot z \cdot F \cdot \pi \cdot \rho_{Me} \cdot R(t+\Delta t) \cdot \sum_{n=1}^{n} PD_n^2(t)} \quad (6)$$

Thus, the pit #n growth rate at time (t=Δt) can be calculated as $$PD_n(t+\Delta t) = PD_n(t) + \frac{A_{Me} \cdot B \cdot \Delta t}{2 \cdot z \cdot F \cdot \pi \cdot \rho_{Me} \cdot R(t+\Delta t) \cdot \sum_{n=1}^{n} PD_n^2(t)} \quad (7)$$

The area under the current time transient curves provides a measure of the pit volume produced during the initiation stage of pit development. By assuming a pit morphology such as for example a hemisphere (903, FIG. 9) the surface area can then be calculated from a simple geometric relationship; e.g. $2/3\pi r^3$=volume and area, $A=2\pi r^2$. Thus, a knowledge of volume (from charge, Faraday's Laws and metal density) can produce a value for r (radius) and hence A (area) at a given time. Rn is measured from the potential and current "noise" outside of the regions of transients (pit initiation) and provides a value of current (from Ohm's Law) that can be allocated to the growing pits (it is assumed that during localized corrosion that all charge is localized with negligible general corrosion). The calculations therefore for individual pit initiation and growth are a matter of converting the data to a current and time that can be integrated at set time periods to provide the charge at each time and hence the volume of metal and hence the penetration rate and also the area of attack.

Localized corrosion, as indicated by the previously described transient Types I-IV, means pitting has happened locally and we can determine the extent of the event, both area and depth of penetration, directly from the current and potential measurements. The surface area of the first pit, $S_1$ is obtained from the charge passed during the initiation period and this charge is converted to area by the use of Faraday's Laws, molar mass of the metal, density and an assumption of geometry of the attack. This initial area is recalculated as t increases and the incremental charge calculated from corrosion rate (Rn) of the pit. As the area is derived from the radius then the determination of the change in depth over time of the pit is also produced. For a combination of more than one pit, there will be a resistance, R, for all the pits, for example according to the sum of the ratios:

$$\frac{1}{R} = \frac{1}{R_1} + \frac{1}{R_2}$$

or more generally:

$$\frac{1}{R} = \sum_{n=1}^{n}\left(\frac{1}{R_n}\right).$$

In this manner, each pit surface area contributes to the overall current as a ratio of the pit area involved where each Rn is given as $$R_n(t + \Delta t) = R(t + \Delta t) \cdot \frac{\sum_{n=1}^{n} PD_n^2(t)}{PD_n^2(t)} \quad (8)$$

That is, charge density is assumed to be equivalent over the total active surface (i.e. active pitting area). Each subsequent initiation of a pitting event shares the total current. The initial pit has the entire general current, the next pit shares the following current (derived from Rn), and each subsequent pit sharing the current proportional to each pits' area.

The method and apparatus herein allow for determinations of changes in the rate of propagation of the depth of pits with time, or penetration rate, from the measured transients Types I-IV. Using this information the approximate mass or volume of metal corroded due to localized corrosion can be determined. The method therefore allows for accurate determination the number of pits that occur and their depth of penetration. The assumption that all or almost all of the corrosion is localized corrosion is strengthened by the fact that the types of corrosion described herein above, especially the 'active' Type I and II transients, directly indicate ongoing localized corrosion. Without the transients that indicate localized corrosion there would be no analysis of corrosion penetration rates.

As previously mentioned, prior art techniques have measured potential and current by alternating measurements of regular periods, for example 30 seconds each. To obtain the most accurate measurements with the method herein, it is desirable to acquire measurements of the current transient throughout the time period that a pitting event occurs, and therefore the measurement of current may last considerably longer than 30 seconds. Transient event monitoring software allowing this monitoring that recognizes types of transients during their occurrence may be provided as part of this method.

Figure 10:
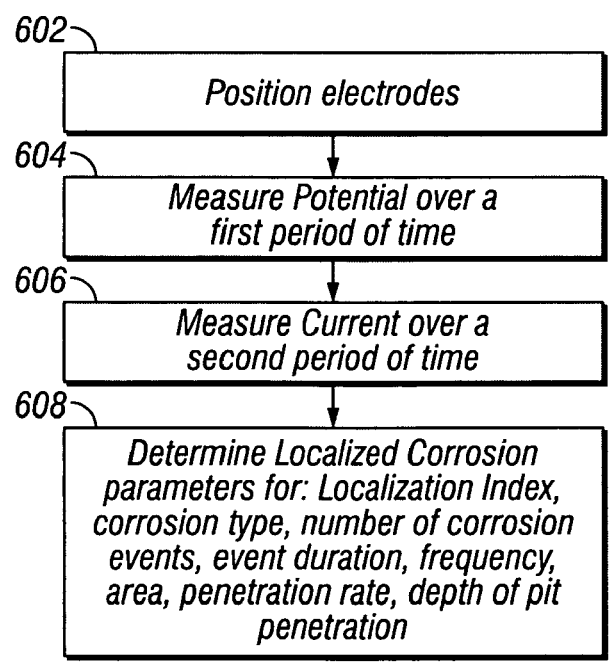
FIG. 10 illustrates a flow chart of one non-limiting embodiment of the method herein.

FIG. 10 is a flow chart illustrating one non-limiting embodiment of the method herein. Electrodes are positioned 602 to acquire data, the potential is measured over a first period of time 604; current is measured over a second period of time 606; and a localized corrosion (number, duration, frequency, rate) of an electrically conductive article is determined 608.

Figure 11:
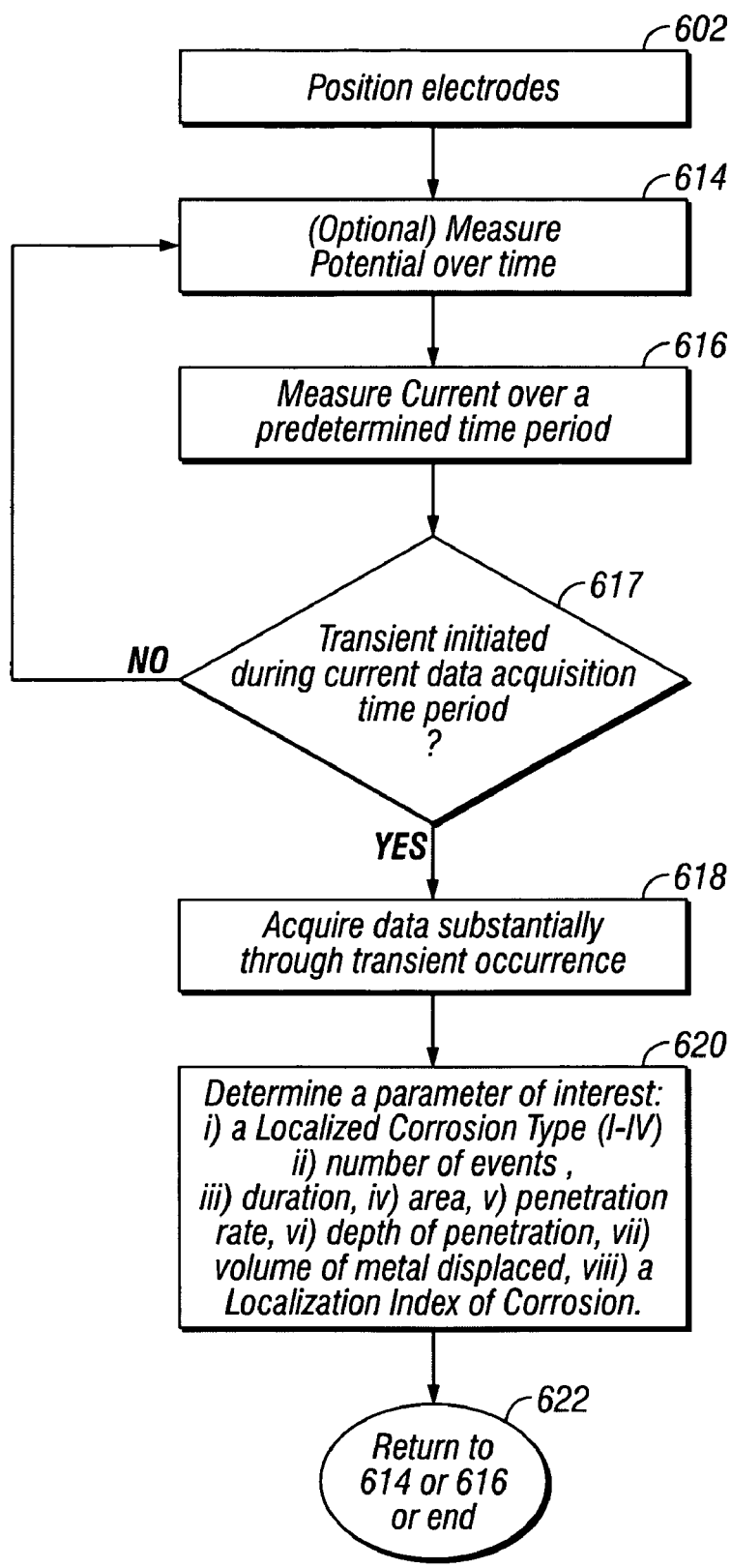
FIG. 11 illustrates a flow chart of an alternate embodiment of the method herein.

FIG. 11 is a flow chart illustrating an alternative embodiment of the method described herein. Electrodes are positioned 602 to acquire data. The potential may be measured over a period of time 614. Whether or not a transient is initiated during the potential data acquisition period is determined 615. If no transient initiates during the potential measurement period, the system may go to 616. If a transient initiates during the period of potential measurement, 618, the method and apparatus provide for acquiring data substantially throughout the time period for which the corrosion event occurs. After acquiring transient data, parameters of interest can be determined from analysis of the transient data 620. For example, the localized corrosion type (I-IV) may be determined, as well as other parameters including the number of pitting events, the area of the pits, the rate of penetration of the events, the depth of penetration of the pits and the volume or mass of the metal corroded during the pitting event. The rate of penetration of pits may be estimated from a time rate of change of the measured current transients. Following the potential measurements, the current is measured over a predetermined period of time 616. Whether or not a transient is initiated during the current data acquisition period is determined 617. If no transient initiates during the current measurement period, the system may cycle back to monitoring potential, 614. If a transient initiates during the period of current measurement, 618, the method provides for acquiring current data substantially throughout the time period for which the corrosion event occurs. After acquiring current transient data, parameters of interest can be determined from analysis of the transient data 620.

Figure 12:
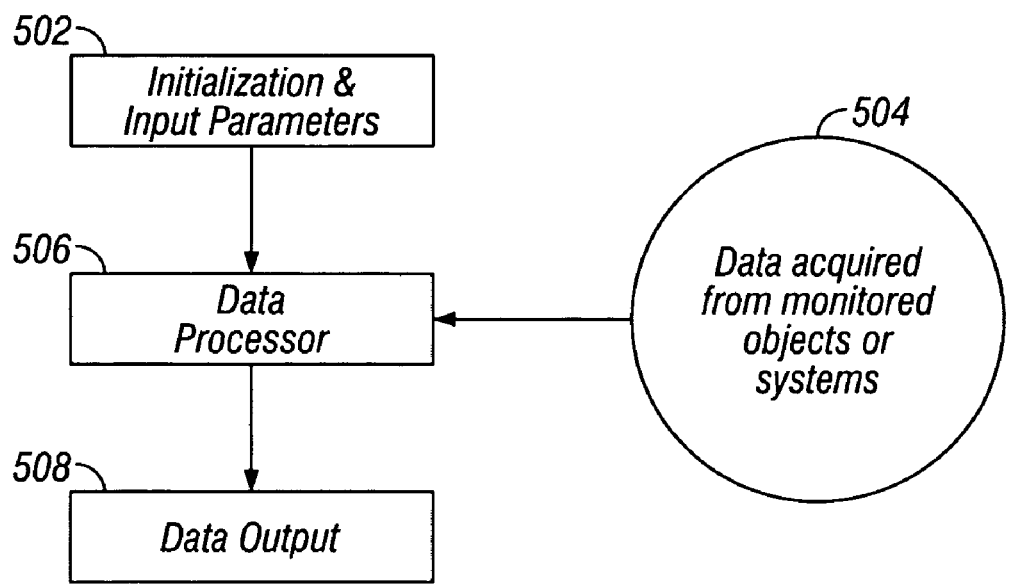
FIG. 12 illustrates schematically one non-limiting embodiment of a system for quantitative transient analysis of localized corrosion.

FIG. 12 illustrates schematically one non-limiting embodiment of a system to implement the methods and goals herein. Initialization and input parameters are chosen for entry 502 to the data processor 506. Data from monitored objects or systems are acquired or prepared for entry 504 to the data processor 506. The data processor 502 may put out data 508 for storage, further processing or display.

Figure 13:
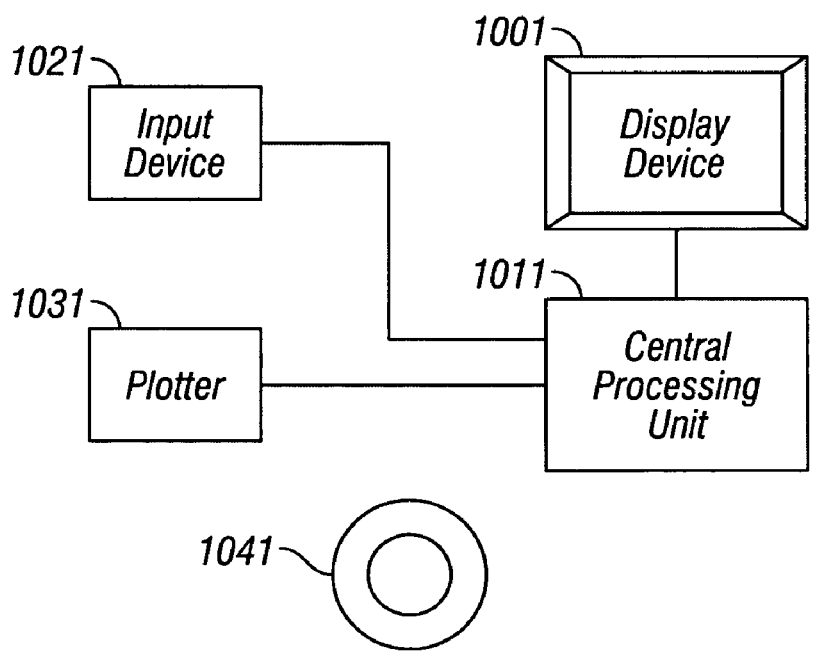
FIG. 13 is a schematic representation of a work station that may be used to write a computer program to carry out the method described herein.

The method and system disclosed herein may be conveniently carried out by writing a computer program to carry out the steps described herein on a work station as illustrated in FIG. 13 or other conventional digital computer system of a type normally used in the industry. The generation of such a program may be performed by those of ordinary skill in the art based on the processes described herein. FIG. 13 illustrates a computer system comprising a central processing unit 1011, a display 1001, an input device 1021, (which devices are known for example, mouse, keyboard, files, etc.) and a plotter 1031. The computer program will normally reside on a storage media (not shown) associated with the central processing unit. The computer program may be transported on a CD-ROM or other storage media shown symbolically as storage medium 1041.

The present apparatus provides for features including an internal potentiostat, a zero resistance ammeter and internal PC (personal computer) or other computing apparatus for monitoring, measuring and analyzing data. The PC may include any operating system and run software for data analysis.

In another embodiment, the method and apparatus are implemented as a set computer executable of instructions on a computer readable medium, comprising ROM, RAM, CD-ROM, Flash RAM or any other computer readable medium, now known or unknown that when executed cause a computer to implement the functions of the present method.

The method and apparatus relate to estimating corrosion parameters on a metallic surface using a unique electrochemical noise technique. A working electrode may be employed where potential created by the corrosion of that electrode in the corrosive fluid is measured relative to a reference electrode over a distinct period of time. The working electrode is then set at the measured potential, and, without applying a potential (ΔV=0), the working electrode is placed in potentiostatic control. Alternatively, or in addition to the potentiostat, the current between the working electrode and the counting electrode is measured for a predetermined period of time. If a transient which may be indicative of pit initiation is detected, the potential or current measurement may be continued substantially through the corrosion event period. The measurement cycle continues or may be repeated after the measurement. Finally, the measured current and potential transient responses are used to determine localized corrosion rates and related parameters of interest.

In order to determine the corrosion rate, the working electrode may be fabricated from the same or reasonably similar material as the item of concern (i.e. the component, article). Generally, the material is a metal or metal alloy. Although the counter electrode can be formed of any material, including the same material as the working electrode, the counter electrode may be comprised of material which is inert in the particular environment of interest. For example, the counter electrode may be platinum, nickel-based (e.g., Hastalloy C276), iron based (e.g., stainless steel) or a chromium-based alloy, or mixtures and alloys thereof, or any other electrically conductive, non-corrosive material. Similar to the counter electrode, the reference electrode can comprise any material, but most conveniently can comprise an inert, electrically conductive material which may be the same or a different material as employed by the counter electrode.

In operation, the working, counter, and reference electrodes are disposed in the same environment as the component of interest, in a spaced relation to one another. A potential between the working and reference electrodes is measured first at open circuit potential for a certain period of time. The period of time, which can be any length of time, is typically less than 1 minute, and may be less than about 10 seconds (sec), with less than about 1 sec being convenient for reduced testing time. At the end of the period of time, a potential equivalent to the measured potential at that time is then applied to the working electrode by switching from open circuit to potentiostatic control. Once potentiostatic conditions have been established, the current between the working electrode and the counter electrode can be measured for a predetermined period (although this predetermined period of time can be set to any amount of time, measurements can continue throughout the duration of a corrosion event is such an event has been detected). A new cycle can then be performed after the potentiostatic current measurement.

Figure 14:
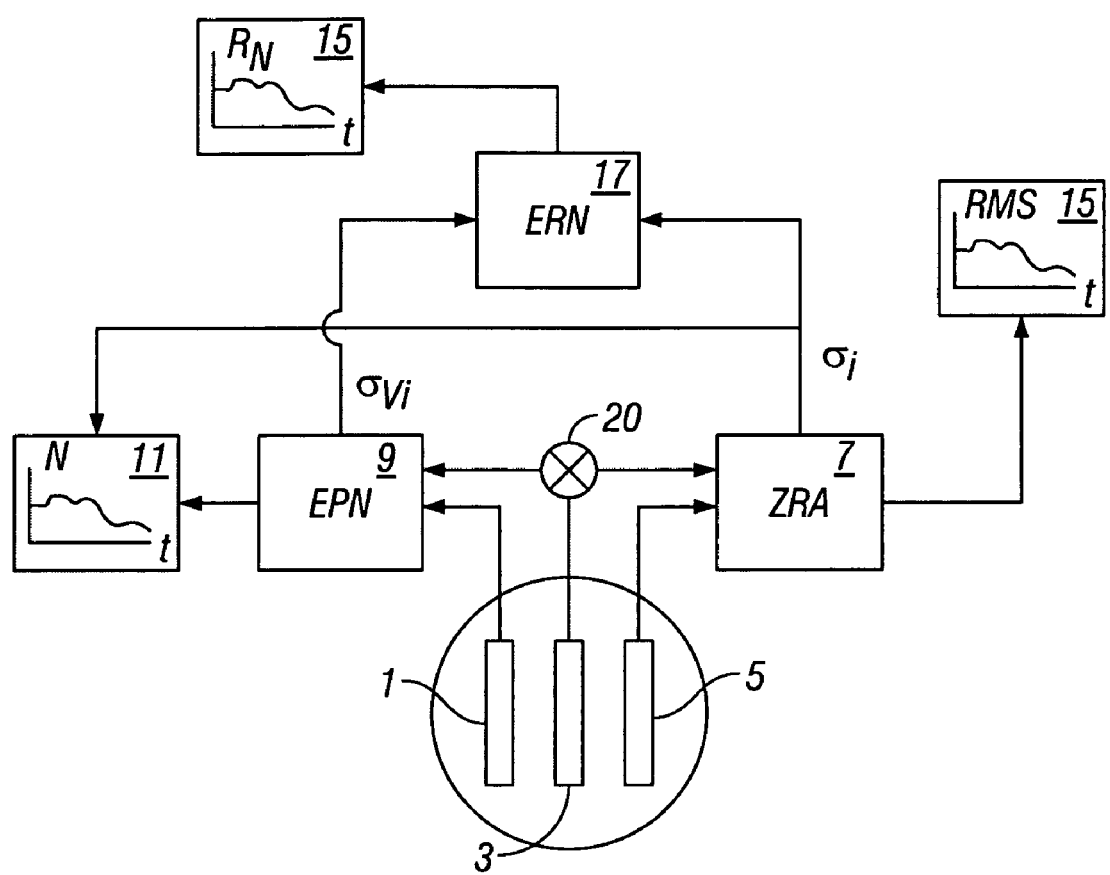
FIG. 14 is a schematic illustration of one embodiment of the apparatus herein.

Referring to FIG. 14, which illustrates a non-limiting embodiment of the present apparatus, a working electrode 3 is disposed between and spaced in relation to both reference electrode 1 and counter electrode 5. The counter electrode 5 and working electrode 3 are connected to a potentiostat 7 which feeds into comparator 17 ($R_N$) and a localized corrosion measurement device 15 capable of measuring localized corrosion as a function of time. Meanwhile, reference electrode 1 and working electrode 3 are connected to electrochemical potential noise monitoring apparatus 9 (i.e., voltmeter) which feeds into comparator 17 and power density analyzer 11. From that input, in combination with input from the electrochemical current noise measuring apparatus 7, localized corrosion rate can be determined. Electrochemical potential noise monitoring apparatus 9 additionally feeds input to comparator 17 to determine general corrosion rate as a function of time.

While various embodiments have been shown and described, various modifications and substitutions may be made thereto without departing from the spirit and scope of the invention. Accordingly, it is to be understood that the present invention has been described by way of illustrations and not limitation.

What is claimed is:

1. A method for calculating localized corrosion of an electrically conductive article comprising:
   (a) placing a working electrode, a reference electrode, and a counter electrode in an environment of interest, wherein the working electrode has substantially the same composition as the electrically conductive article;
   (b) placing the working electrode under potentiostatic control;
   (c) measuring a current transient between the working electrode and the counter electrode;
   (d) switching the working electrode to open circuit potential;
   (e) measuring a potential transient substantially over a duration of a localized corrosion event;
   (f) calculating the localized corrosion based on the measured potential transient and the current transient, where at least one parameter is calculated which parameter is selected from the group consisting of:
      i) the rate of penetration of a pit, based on a time rate of change of the monitored transient; and
      ii) a rate of penetration for multiple pits, based on a sum of ratios:

$$\frac{1}{R} = \sum_{n=1}^{n}\left(\frac{1}{R_n}\right)$$

where each $R_n$ is given substantially as $$R_n(t+\Delta t) = R(t+\Delta t) \cdot \frac{\sum_{n=1}^{n} PD_n^2(t)}{PD_n^2(t)}.$$

2. The method of claim 1 wherein the localized corrosion event is selected from the group consisting of: a) a pit having a depth of penetration, b) a pit having a rate of penetration, and c) a volume of metal displaced.

3. The method of claim 2 wherein the rate of penetration of a pit is calculated based on a time rate of change of the measured potential and current transients.

4. The method of claim 2 wherein a rate of penetration is calculated for multiple pits based on a sum of ratios:

$$\frac{1}{R} = \sum_{n=1}^{n}\left(\frac{1}{R_n}\right)$$

where each $R_n$ is given substantially as $$R_n(t+\Delta t) = R(t+\Delta t) \cdot \frac{\sum_{n=1}^{n} PD_n^2(t)}{PD_n^2(t)}.$$

5. An apparatus for calculating the localized corrosion of an electrically conductive article comprising:
   (a) a working electrode having substantially the same composition of the electrically conductive article;

(b) a reference electrode;
(c) a counter electrode;
(d) a sensor for measuring current transient data between the working electrode and the counter electrode until initiation of a current transient due to a localized corrosion event, wherein the current transient is measured substantially over the duration of the localized corrosion event;
(e) a sensor for measuring potential transient data between the working electrode and the reference electrode until initiation of a potential transient due to a localized corrosion event, wherein the potential transient is measured substantially over the duration of the localized corrosion event; and
(f) a processor for calculating the localized corrosion from the measured current transient and potential transient data, where a parameter is calculated which parameter is selected from the group consisting of:
  i) the rate of penetration of a pit, based on a time rate of change of the monitored transient; and
  ii) a rate of penetration for multiple pits, based on a sum of ratios:

$$\frac{1}{R} = \sum_{n=1}^{n}\left(\frac{1}{R_n}\right)$$

where each $R_n$ is given substantially as $$R_n(t + \Delta t) = R(t + \Delta t) \cdot \frac{\sum_{n=1}^{n} PD_n^2(t)}{PD_n^2(t)}.$$

6. The apparatus of claim 5 wherein the localized corrosion event is selected from the group consisting of: a) a pit having a depth of penetration, b) a pit having a rate of penetration, and c) a volume of metal displaced.

7. The apparatus of claim 5 wherein the rate of penetration of a pit is calculated based on a time rate of change of the measured potential transient and current transient data.

8. The apparatus of claim 5 wherein the geometry of a pit is calculated based on the measured transient.

9. The apparatus of claim 5 wherein the rate of penetration is calculated for multiple pits based on a sum of ratios:

$$\frac{1}{R} = \sum_{n=1}^{n}\left(\frac{1}{R_n}\right)$$

where each $R_n$ is given substantially as $$R_n(t + \Delta t) = R(t + \Delta t) \cdot \frac{\sum_{n=1}^{n} PD_n^2(t)}{PD_n^2(t)}.$$

10. A localized corrosion measuring system for an electrically conductive article in an environment of interest comprising:

a. an electrically conductive fluid-conduit composed of a material of interest;
b. a working electrode which is substantially composed of the material of interest;
c. a counter electrode;
d. a reference electrode; and
e. a measurement system connected to the working electrode, the counter electrode, and the reference electrode for monitoring transient events indicative of localized corrosion, wherein the transient events are monitored between the working electrode, the counter electrode and the reference electrode substantially over the duration of the transient events, where a parameter is calculated which parameter is selected from the group consisting of:
  i) the rate of penetration of a pit, based on a time rate of change of the monitored transient; and
  ii) a rate of penetration for multiple pits, based on a sum of ratios:

$$\frac{1}{R} = \sum_{n=1}^{n}\left(\frac{1}{R_n}\right)$$

where each $R_n$ is given substantially as $$R_n(t + \Delta t) = R(t + \Delta t) \cdot \frac{\sum_{n=1}^{n} PD_n^2(t)}{PD_n^2(t)}.$$

11. The system of claim 10 wherein the counter electrode and the reference electrode are substantially inert in an environment of interest.

12. The system of claim 10 wherein the transient events are selected from the group consisting of: a) a pit having a depth of penetration, b) a pit having a rate of penetration, and c) a volume of metal displaced.

13. The system of claim 10 wherein a rate of penetration of a pit is calculated based on a time rate of change of the monitored transient.

14. The system of claim 10 wherein the electrically conductive fluid-conduit is selected from the group consisting of A) a pipeline; and B) a well bore tubular.

15. The system of claim 10 wherein a rate of penetration is calculated for multiple pits based on a sum of ratios:

$$\frac{1}{R} = \sum_{n=1}^{n}\left(\frac{1}{R_n}\right)$$

where each $R_n$ is given substantially as $$R_n(t + \Delta t) = R(t + \Delta t) \cdot \frac{\sum_{n=1}^{n} PD_n^2(t)}{PD_n^2(t)}.$$

* * * * *